(12) United States Patent
Prasad et al.

(10) Patent No.: US 7,635,469 B2
(45) Date of Patent: *Dec. 22, 2009

(54) MICRONUTRIENT FORMULATIONS FOR HEARING HEALTH

(75) Inventors: Kedar N. Prasad, San Rafael, CA (US); Gerald M. Haase, Greenwood Village, CO (US); William C. Cole, Novato, CA (US)

(73) Assignee: Premier Micronutrient Corporation, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/080,189

(22) Filed: Apr. 1, 2008

(65) Prior Publication Data

US 2008/0187526 A1  Aug. 7, 2008

Related U.S. Application Data

(63) Continuation-in-part of application No. 11/893,894, filed on Aug. 20, 2007, which is a continuation-in-part of application No. 11/032,831, filed on Jan. 11, 2005, which is a continuation of application No. 10/229,271, filed on Aug. 28, 2002, now Pat. No. 6,849,613.

(51) Int. Cl.
*A61K 31/122* (2006.01)
*A61P 27/16* (2006.01)

(52) U.S. Cl. .................................................. 424/94.1
(58) Field of Classification Search .................. 514/52, 514/188, 167, 251, 458, 474, 494, 574, 725; 424/94.1

See application file for complete search history.

(56) References Cited

U.S. PATENT DOCUMENTS

| | | | | |
|---|---|---|---|---|
| 5,292,538 A | * | 3/1994 | Paul et al. | 426/74 |
| 5,561,160 A | * | 10/1996 | Walaszek et al. | 514/574 |
| 5,626,883 A | * | 5/1997 | Paul | 424/605 |
| 5,661,123 A | * | 8/1997 | Stalker et al. | 514/2 |
| 5,895,652 A | * | 4/1999 | Giampapa | 424/195.17 |
| 5,976,568 A | * | 11/1999 | Riley | 424/451 |
| 6,139,872 A | * | 10/2000 | Walsh | 424/464 |
| 6,245,360 B1 | * | 6/2001 | Markowitz | 424/641 |
| 6,291,533 B1 | * | 9/2001 | Fleischner | 514/682 |
| 6,503,529 B1 | * | 1/2003 | Fleischner | 424/439 |
| 6,646,013 B1 | * | 11/2003 | Barker et al. | 514/731 |
| 6,660,293 B2 | * | 12/2003 | Giordano et al. | 424/439 |
| 6,686,340 B2 | * | 2/2004 | Rath | 514/52 |
| 6,693,129 B2 | * | 2/2004 | Rath | 514/474 |
| 6,733,797 B1 | * | 5/2004 | Summers | 424/728 |
| 6,845,777 B2 | * | 1/2005 | Pera | 131/270 |
| 6,849,613 B2 | * | 2/2005 | Prasad et al. | 514/52 |
| 2001/0031744 A1 | * | 10/2001 | Kosbab | 514/54 |
| 2003/0190381 A1 | * | 10/2003 | Bland et al. | 424/757 |
| 2005/0037065 A1 | * | 2/2005 | Kirschner et al. | 424/456 |

\* cited by examiner

*Primary Examiner*—Brian-Yong S Kwon
(74) *Attorney, Agent, or Firm*—Dan M. DeLa Rosa

(57) ABSTRACT

A hearing health micronutrient formulation is provided and the formulation comprises dietary antioxidants and endogenous antioxidants, and the dietary antioxidants are selected from a group consisting essentially of Vitamin A (Palmitate), Vitamin E, Vitamin C (Calcium Ascorbate), Vitamin $D_3$ (Cholecalciferol), B Vitamins, Biotin, Pantothenic Acid (as D-Calcium Pantothenate), Calcium Citrate, Magnesium Citrate, Zinc Glycinate, Selenium (Seleno-L-Methionine), Chromium (as Chromium Picolinate), Mixed Carotenoids and mixtures thereof, and the endogenous antioxidants are selected from a group consisting essentially of N-Acetyl Cysteine (NAC), Coenzyme $Q_{10}$, R-alpha Lipoic Acid, L-Carnitine and mixtures thereof.

5 Claims, No Drawings

US 7,635,469 B2

MICRONUTRIENT FORMULATIONS FOR HEARING HEALTH

RELATED APPLICATION

This application is a continuation-in-part of U.S. application Ser. No. 11/893,894, entitled "Micronutrient Formulations and Related Methods of Manufacture" which was filed on Aug. 20, 2007, which is a continuation-in-part of U.S. application Ser. No. 11/032,831, entitled "Multiple Antioxidant Micronutrients" which was filed on Jan. 11, 2005, which is a continuation of U.S. application Ser. No. 10/229,271, entitled "Multiple Antioxidant Micronutrients" which was filed on Aug. 28, 2002 and issued as U.S. Pat. No. 6,849,613 on Feb. 1, 2005.

BACKGROUND OF THE INVENTION

1. Field of the Invention

The present invention relates to hearing health micronutrient formulations and systems which focus on unique composition combinations and related methods of manufacture. In one embodiment, the hearing health micronutrient formulation comprises: dietary antioxidants and endogenous antioxidants, and the dietary antioxidants are selected from a group consisting essentially of Vitamin A (Palmitate), Vitamin E, Vitamin C (Calcium Ascorbate), Vitamin $D_3$ (Cholecalciferol), B Vitamins, Biotin, Pantothenic Acid (as D-Calcium Pantothenate), Calcium Citrate, Magnesium Citrate, Zinc Glycinate, Selenium (Seleno-L-Methionine), Chromium (as Chromium Picolinate), Mixed Carotenoids and mixtures thereof, and the endogenous antioxidants are selected from a group consisting essentially of N-Acetyl Cysteine (NAC), Coenzyme $Q_{10}$, R-alpha Lipoic Acid, L-Carnitine and mixtures thereof.

2. Description of the Related Art

In the beginning, the earth's atmosphere had no oxygen. Anaerobic organisms, which can live without oxygen, were thriving. About 2.5 million years ago, blue-green algae in the ocean acquired the ability to split water into hydrogen and oxygen and this chemical reaction initiated the release of oxygen into the atmosphere. The increased levels of atmospheric oxygen caused the extinction of many anaerobic organisms owing to oxygen's toxicity. This important biological event also led to the evolution of multicellular organisms, including humans, who utilize oxygen for survival. The content of oxygen in the air gradually increased to the current amounts of about 21 percent in dry air and about 34 percent in water. The use of oxygen by any organism generates free radicals that are toxic. Therefore, during this period of atmospheric oxygenation, organisms must have struggled to survive the sudden exposure to oxygen toxicity. There must have been enormous rearranging of nucleotides in genes to produce specific proteins that could protect organisms against the damage produced by free radicals.

This process eventually led to the production of three antioxidant enzymes. Superoxide dismutase (SOD) requires manganese, copper, or zinc for its biological activity. Mn-SOD is present in mitochondria, whereas Cu-SOD and Zn-SOD are present in the cytoplasm and nucleus of the cell. All three can destroy free radicals and hydrogen peroxide. Another enzyme, catalase, requires iron for its biological activity and it destroys water in cells. Human tissue also contains glutathione peroxidase which requires selenium for its biological activity. It is also responsible for removing hydrogen peroxide.

Although, iron, copper and manganese are essential for the activities of antioxidant enzymes, a slight excess of free iron, copper, or manganese can increase the production of free radicals, and subsequently enhance the risk of various chronic diseases. In addition, organisms, including mammals, consume certain antioxidants that are needed for growth and survival from plants sources. These antioxidants include carotenoids, vitamins A, C, and E, flavonoids, polyphenols, and herbal antioxidants.

Currently, the doses of the antioxidants for the greatest benefit to human health are not well established. Nevertheless, increasing numbers of people are taking some form of supplements in the hope that it will optimize their health. Unfortunately, at present, they rely on advice from health-related magazines, books, advertising, radio and television reports or vitamin store salespeople. In fact, the majority of vitamin/mineral preparations have not given adequate attention to the doses, type, and chemical form of antioxidants, and appropriate minerals and other micronutrients.

SUMMARY OF THE INVENTION

In one embodiment, the present invention provides for a micronutrient formulation, the formulation comprises: a first composition comprising alpha tocopherol and derivative esters of alpha tocopherol, the derivative esters of alpha tocopherol being selected from a group consisting essentially of alpha tocopheryl acetate, alpha tocopheryl palmitate, alpha tocopheryl succinate, alpha tocopheryl nicotinate and mixtures thereof, a second composition comprising vitamin A and natural-mixed carotenoids; and a third composition comprising calcium ascorbate. For purposes of this invention, natural-mixed carotenoids are defined as a natural extract of the algae species *Dunaliella salina*, the majority of which is beta carotene that contains various other natural carotenoids present in smaller amounts.

In a further embodiment, the method of the present invention wherein the percentage of each composition is as follows: the first composition is from about 1 to about 50% of the formulation; the second composition is from about 1 to about 50% of the formulation; and the third composition is from about 1 to about 50% of the formulation.

In another embodiment, the formulation further comprises a fourth composition, and the fourth composition is selected from a group consisting essentially of B-vitamins, selenium, zinc, magnesium, chromium and mixtures thereof. In yet another embodiment, the first, second, third and fourth compositions function as dietary micronutrients. For purposes of this invention, the term "dietary micronutrients" are defined as nutrients, including but not limited to vitamins and minerals that are consumed through the diet in small amounts and are distinct from dietary macronutrients which are defined as fats, proteins and carbohydrates. Dietary micronutrients include, but are not limited to tocopherols and tocopheryl esters (Vitamin E), Vitamin A, Vitamin C, Vitamin D, B-Vitamins, selenium, calcium, magnesium, zinc, carotenoids (e.g. beta carotene), and chromium.

In still another embodiment, the calcium ascorbate in the third composition is a source of vitamin C. In still yet another embodiment, the formulation further comprises a fifth composition, and the fifth composition is selected from a group consisting essentially of alpha lipoic acid, co-enzyme $Q_{10}$, L-carnitine, n-acetyl cysteine and mixtures thereof. In a further embodiment, the fifth composition functions as an endogenous micronutrient. For purposes of this invention, the term "endogenous micronutrients" are defined as nutrients that are normally produced by the body. Due to factors such as aging, disease, physical activity level and environmental stressors, optimal amounts of these endogenous micronutrients may no longer be present in the body and need to be provided through supplementation. Endogenous micronutrients can be included in dietary supplements from synthetic or natural sources. Endogenous micronutrients include, but are not limited to lipoic acid, N-acetyl cysteine, nicotinamide adenine dinucleotide (NADH), 1-carnitine, and coenzyme Q10.

In another further embodiment, the formulation further comprises reduced nicotinamide adenine dinucleotide.

In yet a further embodiment, the present invention provides for a micronutrient formulation system, the system comprises: a first composition comprising alpha tocopheryl and derivative esters of alpha tocopherol, the derivative esters of alpha tocopherol being selected from a group consisting essentially of alpha tocopheryl acetate, alpha tocopheryl palmitate, alpha tocopheryl succinate, alpha tocopheryl nicotinate and mixtures thereof; a second composition comprising vitamin A and natural-mixed carotenoids; a third composition comprising calcium ascorbate; a fourth composition selected from a group consisting essentially of B-vitamins, selenium, zinc, magnesium, chromium and mixtures thereof; and a fifth composition selected from a group consisting essentially of alpha lipoic acid, co-enzyme Q10, L-carnitine, n-acetyl cysteine and mixtures thereof, wherein said formulation is without iron, copper and manganese.

In still a further embodiment, the formulation system of the present invention wherein the first composition is from about 1 to about 50% of the formulation; the second composition is from about 1 to about 50% of the formulation; the third composition is from about 1 to about 50% of the formulation; the fourth composition is from about 1 to about 50% of the formulation; and the fifth composition is from about 1 to about 50% of the formulation.

In still yet a further embodiment, the formulation system of the present invention is consumed by the user at least twice per day.

In another further embodiment, the present invention provides for a method of manufacturing a micronutrient formulation comprising: admixing a first composition comprising alpha tocopheryl and derivative esters of alpha tocopherol, and the derivative esters of alpha tocopherol being selected from a group consisting essentially of alpha tocopheryl acetate, alpha tocopheryl palmitate, alpha tocopheryl succinate, alpha tocopheryl nicotinate and mixtures thereof; and then admixing a second composition comprising vitamin A and natural-mixed carotenoids; and then admixing a third composition comprising calcium ascorbate; and then admixing a fourth composition comprising selected from a group consisting essentially of B-vitamins, selenium, zinc, magnesium, chromium and mixtures thereof; and then admixing with a fifth composition selected from a group consisting essentially of alpha lipoic acid, co-enzyme Q10, L-carnitine, n-acetyl cysteine and mixtures thereof. In one embodiment, the individual compositions are first admixed or combined and then the first composition is admixed with the second and then the first and second compositions are then admixed with the third composition; then the first second and third mixed compositions are then admixed with the fourth composition and then the fifth composition is admixed at the end. In another embodiment, the compositions are all admixed together. In still another embodiment, the compositions can be added in any random order.

In a further embodiment, the method of the present invention wherein the percentage of each composition is as follows: the first composition is from about 1 to about 50% of the formulation; the second composition is from about 1 to about 50% of the formulation; the third composition is from about 1 to about 50% of the formulation; the fourth composition is from about 1 to about 50% of the formulation; and the fifth composition is from about 1 to about 50% of the formulation.

In a further embodiment, the method of the present invention wherein the percentage of each composition is as follows: the first composition is from about 1 to about 30% of the formulation; the second composition is from about 1 to about 30% of the formulation; the third composition is from about 1 to about 20% of the formulation; the fourth composition is from about 1 to about 20% of the formulation; and the fifth composition is from about 1 to about 20% of the formulation.

In another further embodiment, the method of the present invention further comprises admixing reduced nicotinamide adenine dinucleotide. In yet another embodiment, the formulation is consumed twice a day. In still yet another embodiment, the formulation is without iron, copper and manganese.

In a further embodiment, the formulation is designed to prevent excess production of free radicals by the administration of the formulation to a patient.

In another further embodiment, the present invention relates to a micronutrient formulation that comprises: a first composition comprising Vitamin A, Vitamin C, Vitamin E and beta carotene; and a second composition comprising lipoic acid. In yet a further embodiment, the formulation further comprises a third composition, and the third composition is selected from a group consisting essentially of co-enzyme Q10, L-carnitine, n-acetyl cysteine and mixtures thereof. In still a further embodiment, the formulation is consumed by the user at least twice per day.

In further embodiment, the present invention is directed to a method for optimizing the health of humans according to their age and sex comprising administering to said humans a daily dose of a multiple antioxidant micronutrient composition comprising vitamin A (palmitate), beta-carotene (from natural *D. salina*), vitamin C (calcium ascorbate), natural source vitamin E including both d-alpha tocopherol and d-alpha tocopheryl acid succinate, thiamine mononitrate, riboflavin, niacinamide ascorbate, d-calcium pantothenate, pyridoxine hydrochloride, cyanocobalamin, folic acid (folacin), d-biotin, selenium (1-seleno methionine), chromium picolinate, zinc glycinate, calcium citrate and magnesium citrate.

For persons over the age of about 51, the composition preferably further comprises one or more of co-enzymeQ10, N-acetyl cysteine and alpha lipoic acid. In another embodiment, an increased amount of vitamin D, calcium and magnesium is added for women over the age of about 36.

In another embodiment, the present invention provides for a micronutrient formulation consisting essentially of:
Vitamin A (Palmitate),
Vitamin E,
Vitamin C (Calcium Ascorbate),
Vitamin $D_3$ (Cholecalciferol),
B Vitamins
Biotin
Pantothenic Acid (as D-Calcium Pantothenate)
Calcium Citrate
Magnesium Citrate
Zinc Glycinate
Selenium (Seleno-L-Methionine)
Chromium (as Chromium Picolinate)
N-Acetyl Cysteine (NAC)
Coenzyme $Q_{10}$
R-alpha Lipoic Acid
L-Carnitine and
Natural Mixed Carotenoids.

In another embodiment, Vitamin E is selected from a group consisting essentially of alpha tocopherol and derivative esters of alpha tocopherol, and mixtures thereof. In still another embodiment, the derivative esters of alpha tocopherol are selected from a group consisting essentially of alpha tocopheryl acetate, alpha tocopheryl palmitate, alpha tocopheryl succinate, alpha tocopheryl nicotinate and mixtures thereof.

In yet another embodiment, B Vitamins are selected from a group consisting essentially of Vitamin $B_1$ (Thiamine Mononitrate), Vitamin $B_2$ (Riboflavin), Vitamin $B_3$ (Niacinamide Ascorbate), Vitamin $B_6$ (Pyridoxine Hydrochloride), Folic Acid, Vitamin $B_{12}$ (Cyanocobalamln) and mixtures thereof.

In still yet another embodiment, the mixed carotenoids are selected from a group consisting essentially of natural sources of algae (D. Salina), alpha carotene, beta carotene, gamma carotene, lutein, lycopene, xynthines, beta-cryptoxanthin, zeaxanthin, astaxanthin, phytoene, canthaxanthin, fucoxanthin and mixtures thereof.

In a further embodiment, the formulation is designed for hearing health and consumed by the user at least twice per day. In still a further embodiment, the formulation is consumed by the user at a timing made for body tissue saturation prior to exposure to a hearing hazard, during exposure to a hearing hazard and for hearing loss caused by aging.

In yet a further embodiment, the formulation is consumed by the user for long term maintenance after exposure to a hearing hazard. In still yet a further embodiment, the long term maintenance is from about at least one week to about life long.

In still yet a further embodiment, the present invention provides for a formulation consists essentially of:

| | |
|---|---|
| Vitamin A (Palmitate) | 5000 IU |
| Vitamin E | 400 IU |
| Vitamin C (Calcium Ascorbate) | 1500 mg |
| Vitamin $D_3$ (Cholecalciferol) | 400 IU |
| Vitamin $B_1$ (Thiamine Mononitrate) | 4 mg |
| Vitamin $B_2$ (Riboflavin) | 5 mg |
| Vitamin $B_3$ (Niacinamide Ascorbate) | 30 mg |
| Vitamin $B_6$ (Pyridoxine Hydrochloride) | 5 mg |
| Folic Acid | 800 mcg |
| Vitamin $B_{12}$ (Cyanocobalamln) | 10 mcg |
| Biotin | 200 mcg |
| Pantothenic Acid (as D-Calcium Pantothenate) | 10 mg |
| Calcium Citrate | 250 mg |
| Magnesium Citrate | 125 mg |
| Zinc Glycinate | 15 mg |
| Selenium (Seleno-L-Methionine) | 100 mcg |
| Chromium (as Chromium Picolinate) | 50 mcg |
| N-Acetyl Cysteine (NAC) | 300 mg |
| Coenzyme $Q_{10}$ | 60 mg |
| R-alpha Lipoic Acid | 60 mg |
| L-Carnitine | 150 mg |
| Natural Mixed Carotenoids | 15 mg |

In another further embodiment, the present invention relates to a formulation for hearing health, and the formulation comprising dietary micronutrients and endogenous antioxidants. The dietary antioxidants is selected from a group consisting essentially of Vitamin A (Palmitate), Vitamin E, Vitamin C (Calcium Ascorbate), Vitamin $D_3$ (Cholecalciferol), B Vitamins, Biotin, Pantothenic Acid (as D-Calcium Pantothenate), Calcium Citrate, Magnesium Citrate, Zinc Glycinate, Selenium (Seleno-L-Methionine), Chromium (as Chromium Picolinate), Mixed Carotenoids and mixtures thereof, and the endogenous antioxidants are selected from a group consisting essentially of N-Acetyl Cysteine (NAC), Coenzyme $Q_{10}$, R-alpha Lipoic Acid, L-Carnitine and mixtures thereof, wherein the formulation is designed for hearing health. For purposes of this invention, dietary micronutrients include micronutrients and antioxidants.

In another embodiment, the present invention provides for a hearing health formulation comprising first and second compositions, said first composition consisting essentially of:
Vitamin A (Palmitate) from about 3,000 to about 5000 IU
Vitamin E from about 50 to about 600 IU
Vitamin C (Calcium Ascorbate) from about 200 to about 800 mg
Vitamin $D_3$ (Cholecalciferol) from about 400 to about 600 IU
Vitamin $B_1$ (Thiamine Mononitrate) from about to 2 about 10 mg
Vitamin $B_2$ (Riboflavin) from about 2 to about 20 mg
Vitamin $B_3$ (Niacinamide Ascorbate) from about 15 to about 200 mg
Vitamin $B_6$ (Pyridoxine Hydrochloride) from about 2 to about 10 mg
Folic Acid from about 400 to about 1500 mcg
Vitamin $B_{12}$ (Cyanocobalamln) from about 5 to about 20 mcg
Biotin from about 100 to about 500 mcg
Pantothenic Acid (as D-Calcium Pantothenate) from about 5 to about 30 mg
Calcium Citrate from about 100 to about 500 mg
Magnesium Citrate from about 100 to about 300 mg
Zinc Glycinate from about 10 to about 40 mg
Selenium (Seleno-L-Methionine) from about 50 to about 300 mcg
Chromium (as Chromium Picolinate) from about 50 to about 200 mcg, and a second composition consisting essentially of:
N-Acetyl Cysteine (NAC) from about 100 to about 800 mg
Coenzyme $Q_{10}$ from about 20 to about 300 mg
R-alpha Lipoic Acid from about 15 to about 200 mg
L-Carnitine from about 100 to about 400 mg
Natural Mixed Carotenoids from about 5 to about 45 mg and wherein said formulation is designed to treat hearing hazards.

In a further embodiment, Vitamin E is selected from a group consisting essentially of d-alpha Tocopheryl Succinate from about 50 to about 600 IU, d-alpha Tocopheryl Acetate from about 50 to about 300 IU and mixtures thereof, and the mixed carotenoids are selected from a group consisting essentially of natural sources of algae, alpha carotene, beta carotene, gamma carotene, lutein, lycopene, xynthines and mixtures thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The specific example below will enable the invention to be better understood. However, they are given merely by way of guidance and do not imply any limitation. Generally healthy patients on an optimal preventive health formula are routinely categorized by age and sex, i.e., Ages 5 to 12, male and female; Ages 13 to 17 years, male and female; Ages 18 to 35 years, male and female; Ages 36 to 50 years, males; Ages 36 to 50 years, female; Ages 51 to 65 years, male; Ages 51 to 65, female; Ages 66 and over, male; and Ages 66 and over, female.

Most commercially available multiple supplement formulations contain iron, copper, and/or manganese. It is well known that these substances actively generate free radicals when combined with vitamin C. In addition, these minerals are more easily absorbed from the intestinal tract in the presence of antioxidants, such as vitamin C, and thereby increase the body stores of these minerals. Increased iron stores have been associated with many chronic human conditions, including heart disease, cancer and neurological diseases. Therefore, the addition of iron, copper or manganese to any multiple antioxidant preparation has no scientific merit for optimal health or disease prevention. Only in cases where a person has iron-deficiency anemia is a short-term iron supplement essential.

Many commercially available preparations contain heavy metals such as boron, vanadium, zirconium and molybdenum. Sufficient amounts of these metals are obtained from the diet and the daily consumption of excess amounts over long periods of time can be neurotoxic.

Many commercial preparations contain inositol, methionine and choline in varying amounts, e.g., 30 mg to 60 mg. These small doses serve no useful purpose for improving health because 400 mg to 1,000 mg of these nutrients are obtained daily from even the most minimal diet.

Para-aminobenzoic acid (PABA) is present in some multiple vitamin preparations. PABA has no biologic function in mammalian cells and can block the antibacterial effect of sulfonamides. Therefore, the effectiveness of a sulfonamide may be reduced in some patients being treated for bacterial infection.

Commercially sold multiple antioxidant preparations often contain varying amounts of N-acetyl cysteine or alpha lipoic acid. These nutrients are utilized because they are known to increase glutathione levels in cells. Reduced glutathione is a powerful antioxidant and actively protects both normal and cancer cells against radiation damage. Many cancer patients take antioxidant supplements without the knowledge of their oncologists. Therefore, the consumption of antioxidant preparations containing N-acetyl cysteine or alpha lipoic acid by these patients undergoing radiation therapy could interfere with important anti-cancer treatment.

The addition of both beta-carotene and vitamin A to any multiple vitamin preparation is essential, because beta-carotene not only acts as a precursor of vitamin A, but also performs important biological functions that cannot be performed by vitamin A. Beta-carotene increases the expression of the connexin gene, which codes for a gap junction protein that is necessary for maintaining the normal cellular phenotype. While other carotenoids, such as, lycopene, xanthophylls, and lutein, are also important for health, they can be obtained from an adequate diet with tomato (lycopene), spinach (lutein), and paprika (xanthophylls) in amounts higher than those that can be supplied from supplements. Therefore, the addition of a few milligrams of lycopene, xanthophylls, and lutein to any multiple vitamin preparation serves no useful purpose for health or disease prevention.

The proper ratio of two forms of vitamin E, d-alpha tocopherol, which is normally present in the body, and d-alpha succinate, to a multiple antioxidant preparation is essential. Alpha tocopheryl succinate is the most effective form of vitamin E inside the cells, where as alpha tocopherol can readily act as an antioxidant in the intestinal tract and in the extracellular environment of the body. Alpha-tocopherol at doses of 20-60 μg/ml can stimulate the immune system, while the beta, gamma, and delta forms at similar doses can inhibit the immune system. This effect of these forms of tocopherol may not be related to their antioxidant action and, since they are less effective than alpha tocopherol, their supplementation is not recommended.

Tocotrienols are also antioxidants, but they may inhibit cholesterol synthesis. Since this activity is not beneficial in healthy individuals, prolonged consumption of tocotrienols as a supplement is not optimal.

Vitamin C is usually administered as ascorbic acid, which can cause stomach upset, diarrhea and other complications in some individuals. However, using the calcium ascorbate form is most suitable because it is non-acidic and has not been shown to produce negative side effects. The use of potassium ascorbate and magnesium ascorbate in any vitamin preparation is unnecessary. Also, any multiple micronutrient preparation should include adequate amounts of B-vitamins (2-3 times of RDA) and appropriate minerals.

A supplement that attempts to include all antioxidants or micronutrients without regard to age, sex, general health and disease status, is irrational and cannot be recommended. It appears more appropriate to utilize a basic antioxidant formulation that contains necessary nutrients for optimal health, and then supplement that product with additional nutrients based on the above individual factors.

A balanced diet may be sufficient for normal growth, but supplemental micronutrients, including antioxidants, are important for optimal health. With the current typical American diet, one would have difficulty eating fresh fruit and vegetables daily in the amounts and at the frequencies each day necessary to maintain sustained optimal levels of beta-carotene and vitamins, A, C and E in body tissues. In addition, when one travels away from home the availability of these vital foods may be limited. While some scientists believe that a balanced diet is sufficient for maintaining optimal health, many studies suggest that most foods contain naturally occurring toxic, as well as protective, substances. While a balanced diet may prevent vitamin deficiency, it may not be sufficient for disease prevention since the concept of "balance" may vary markedly from one individual to another. In addition, environmental sources of toxins (such as pesticides) may well vary from region to region.

Another advantage of the supplements of the present invention is that they can be consumed at the most appropriate time to maximize their effectiveness in preventing the formation of toxic chemicals (mutagens and carcinogens) in the gastrointestinal tract during digestion. For example, if vitamins C and E are taken immediately before eating nitrite-rich food, the formation of mutagenic nitrosamines in the stomach may be reduced, whereas taking these vitamins a few hours after such a meal may not be effective in reducing the formation of this cancer-causing substance. Furthermore, studies have demonstrated that levels of fecal mutagens (a possible source of cancer) in people who regularly eat meat are much higher than in vegetarians. Ingestion of vitamins C and E has been shown to reduce the levels of mutagens in feces. Therefore, these supplements should be taken before, or right after, eating meat, whereas consuming them several hours after such a meal may not be as effective.

The risk of chronic illness may depend upon the relative consumption of protective versus toxic substances. If the daily intake of protective substances is higher than toxic agents, the incidence of chronic illness may be reduced. Since we know very little about the relative levels of toxic and protective substances in any diet, a daily supplement of micronutrients including antioxidants would assure a higher level of preventive protection.

Free radicals are examples of primary agents involved in increasing the risk of cancer, heart disease and neurological disease. If they damage normal dividing cells, the risk of cancer is increased. If they damage non-dividing cells, such as neurons, the risk of neurological disease is enhanced. Therefore, quenching free radicals with antioxidants is important for the maintenance of optimal health.

The basic micronutrient formulation of the present invention satisfies all of the required components previously outlined and provides a foundation for a maximally effective preventive formula for otherwise healthy people. Since the biologic half-life of most micronutrients is much less than 12 hours, it is essential to take these supplements twice a day.

In older age groups (greater than 50 years), the addition of co-enzyme Q10 is important because it may improve mitochondrial function and increase energy level. In addition, the likelihood of mitochondrial damage increases with age.

Furthermore, the sulfhydryl compounds, such as glutathione, are important antioxidants that protect cells against free radical damage. Although glutathione levels decrease with aging, it cannot be taken as a supplement because it is completely destroyed during digestion. Therefore, N-acetyl cysteine and alpha lipoic acid, which increase cellular levels of glutathione, are recommended for older individuals.

To reduce the risk of osteoporosis in women, an appropriate calcium/magnesium preparation with vitamin D is required. The citrate form is most efficiently absorbed where as the oxide form is not. The presence of vitamin D increases the absorption of calcium from the intestinal tract. This supplementation is especially important after menopause where the loss of calcium increases with age.

EXAMPLE 1

Suggested Daily Formulation

| Ages 5-12 years, male and female: | |
|---|---|
| Vitamin A (palmitate) | 2,500 I.U. |
| Beta-carotene (from natural *D. salina*) | 7.5 mg |
| Buffered Vitamin C (calcium ascorbate) | 100 mg |
| Vitamin D-3 (cholecalciferol) | 200 I.U. |
| Natural SourceVitamin E | |
| (d-alpha tocopherol) | 25 I.U. |
| (d-alpha tocopheryl acid succinate) | 25 I.U. |
| Thiamine mononitrate | 2 mg |
| Riboflavin | 2 mg |
| Niacinamide | 10 mg |
| d-Calcium Pantothenate | 5 mg |
| Pyridoxine hydrochloride | 2 mg |
| Cyanocobalamin | 5 mcg |
| Folic Acid (Folacin) | 400 mcg |
| d-Biotin | 100 mcg |
| Calcium (Calcium citrate) | 100 mg elemental calcium |
| Magnesium (Magnesium citrate) | 50 mg elemental magnesium |
| Zinc (Zinc glycinate) | 7.5 mg elemental zinc |
| Selenium (l-seleno-methionine) | 50 mcg elemental selenium |
| Chromium (Chromium picolinate) | 25 mcg elemental chromium |

Other Ingredients Raspberry juice, black current juice, natural fruit acids, natural colors, natural fruit sugars.

Free of: Artificial sweeteners, Starch, Lactose, Milk products, wheat, corn, soy, egg, yeast, artificial colors, and preservatives.

Example 1 relates to a formulation targeted at young males and females, 5-12 years of age. This youth formula is a unique blend of dietary micronutrients with appropriate dosages for youths and an appropriate spectrum of B-vitamins for youths of both genders.

EXAMPLE 2

Suggested Daily Formulation

| Ages 13-17 years, male and female: | |
|---|---|
| Vitamin A (palmitate) | 2,500 I.U. |
| Beta-carotene (from natural *d. salina*) | 7.5 mg |
| Vitamin C (calcium ascorbate) | 250 mg |
| Vitamin D-3 (cholecalciferol) | 200 I.U. |
| Natural source Vitamin E | |
| (d-alpha tocopherol) | 50 I.U. |
| (d-alpha tocopheryl acid succinate) | 50 I.U. |
| Thiamine mononitrate | 2 mg |
| Riboflavin | 2.5 mg |
| Niacinamide ascorbate | 15 mg |
| d-Calcium pantothenate | 5 mg |
| Pyridoxine hydrochloride | 2.5 mg |
| Cyanocobalamin | 5 μg |
| Folic acid (folacin) | 400 μg |
| d-Biotin | 100 μg |
| Selenium (l-seleno methionine) | 50 μg |
| Chromium picolinate | 25 μg |
| Zinc glycinate | 7.5 mg |
| Calcium citrate | 125 mg |
| Magnesium citrate | 62.5 mg |

Example 2 relates to a formulation targeted at males and females, 13-17 years of age. This teenage formula is a unique blend of dietary micronutrients with appropriate dosages for teenagers and an appropriate spectrum of B-vitamins for teenagers of both genders.

EXAMPLE 3

Suggested Daily Formulation

| Ages 18-35 years, male and female: | |
|---|---|
| Vitamin A (palmitate) | 5,000 I.U. |
| Beta-carotene (from natural *d. salina*) | 15 mg |
| Vitamin C (calcium ascorbate) | 500 mg |
| Vitamin D-3 (cholecalciferol) | 400 I.U. |
| Natural source vitamin E | |
| (d-alpha tocopherol) | 100 I.U. |
| (d-alpha tocopheryl acid succinate) | 100 I.U. |
| Thiamine mononitrate | 4 mg |
| Riboflavin | 5 mg |
| Niacinamide ascorbate | 30 mg |
| d-Calcium pantothenate | 10 mg |
| Pyridoxine hydrochloride | 5 mg |
| Cyanocobalamin | 10 μg |
| Folic acid (folacin) | 800 μg |
| d-Biotin | 200 μg |
| Selenium (l-seleno methionine) | 100 μg |
| Chromium picolinate | 50 μg |
| Zinc glycinate | 15 mg |
| Calcium citrate | 250 mg |
| Magnesium citrate | 125 mg |

Example 3 relates to a formulation targeted at males and females, 18-35 years of age. This young adult formula is a unique blend of dietary micronutrients with appropriate dosages for young adults and increases dosages for healthy adults of both genders.

EXAMPLE 4

Suggested Daily Formulation

| Ages 36-50 years, male: | |
|---|---|
| Vitamin A (palmitate) | 5,000 I.U. |
| Beta-carotene (from natural *d. salina*) | 15 mg |
| Vitamin C (calcium ascorbate) | 1,500 mg |
| Vitamin D-3 (cholecalciferol) | 400 I.U. |
| Natural source vitamin E | |
| (d-alpha tocopherol) | 100 I.U. |
| (d-alpha tocopheryl acid succinate) | 300 I.U. |
| Thiamine mononitrate | 4 mg |
| Riboflavin | 5 mg |
| Niacinamide ascorbate | 30 mg |
| d-Calcium pantothenate | 10 mg |
| Pyridoxine hydrochloride | 5 mg |
| Cyanocobalamin | 10 µg |
| Folic acid (folacin) | 800 µg |
| d-Biotin | 200 µg |
| Selenium (l-seleno methionine) | 100 µg |
| Chromium picolinate | 50 µg |
| Zinc glycinate | 15 mg |
| Calcium citrate | 250 mg |
| Magnesium citrate | 125 mg |

Example 4 relates to a formulation targeted at males, 36-50 years of age. This male middle-aged adult formula is a unique blend of dietary and endogenous micronutrients formulated to account for the needs of middle-aged adults.

In another embodiment, the following may also added to Example 4:

| N-acetyl cysteine | 250 mg |
|---|---|
| Coenzyme Q10 | 45 mg |
| α-Lipoic acid | 45 mg |
| L-carnitine | 100 mg |

EXAMPLE 5

Suggested Daily Formulation

For women, the following supplements should be added:

| Calcium citrate | 1,500 mg |
|---|---|
| Magnesium citrate | 750 mg |
| Vitamin D | 100 I.U. |

Example 5 relates to a formulation targeted at females, 36-50 years of age. This middle-aged female adult formula is a combination of dietary and endogenous micronutrients with various additives such as calcium for proper bone health and bone density.

EXAMPLE 6

Suggested Daily Formulation

| Ages 51-65 years, male: | |
|---|---|
| Vitamin A (palmitate) | 5,000 I.U. |
| Beta-carotene (from natural *d. salina*) | 15 mg |
| Vitamin C (calcium ascorbate) | 1,500 mg |
| Vitamin D-3 (cholecalciferol) | 400 I.U. |
| Natural source vitamin E | |
| (d-alpha tocopherol) | 100 I.U. |
| (d-alpha tocopheryl acid succinate) | 300 I.U. |
| Thiamine mononitrate | 4 mg |
| Riboflavin | 5 mg |
| Niacinamide ascorbate | 30 mg |
| d-Calcium pantothenate | 10 mg |
| Pyridoxine hydrochloride | 5 mg |
| Cyanocobalamin | 10 µg |
| Folic acid (folacin) | 800 µg |
| d-Biotin | 200 µg |
| Selenium (l-seleno methionine) | 100 µg |
| Chromium picolinate | 50 µg |
| Zinc glycinate | 15 mg |
| Calcium citrate | 250 mg |
| Magnesium citrate | 125 mg |
| Co-enzyme Q10 | 30 mg |
| n-Acetyl cysteine | 250 mg |

Example 6 relates to a formulation targeted at males, 51-65 years of age. This senior male adult formula is a combination of dietary and endogenous micronutrients with appropriate increases of the relevant families of antioxidants to account for the increased needs of the older population.

In a further embodiment, the co-enzyme Q10 in Example 6 is changed from 30 mg to 60 mg and the following are also added:

| α-Lipoic acid | 45 mg |
|---|---|
| L-carnitine | 150 mg |

EXAMPLE 7

Suggested Daily Formulation

For women, the following supplements should be added:

| Calcium citrate | 1,500 mg |
|---|---|
| Magnesium citrate | 750 mg |
| Vitamin D | 100 I.U. |

Example 7 relates to a formulation targeted at females, 51-65 years of age. This senior female adult formula is a combination of dietary and endogenous micronutrients with appropriate increases of the relevant families of antioxidants to account for the increased needs of the older population and with various additives such as calcium for proper bone health and bone density.

EXAMPLE 8

Suggested Daily Formulation

| Age 66 and over, male: | |
|---|---|
| Vitamin A (palmitate) | 5,000 I.U. |
| Beta-carotene (from natural d. salina) | 15 mg |
| Vitamin C (calcium ascorbate) | 2,500 mg |
| Vitamin D-3 (cholecalciferol) | 400 I.U. |
| Natural source vitamin E | |
| (d-alpha tocopherol) | 100 I.U. |
| (d-alpha tocopheryl acid succinate) | 300 I.U. |
| Thiamine mononitrate | 4 mg |
| Riboflavin | 5 mg |
| Niacinamide ascorbate | 30 mg |
| d-Calcium pantothenate | 10 mg |
| Pyridoxine hydrochloride | 5 mg |
| Cyanocobalamin | 10 μg |
| Folic acid (folacin) | 800 μg |
| d-Biotin | 200 μg |
| Selenium (l-seleno methionine) | 100 μg |
| Chromium picolinate | 50 μg |
| Zinc glycinate | 15 mg |
| Calcium citrate | 250 mg |
| Magnesium citrate | 125 mg |
| Co-enzyme Q10 | 30 mg |
| n-Acetyl cysteine | 250 mg |
| Alpha lipoic acid | 30 mg |

Example 8 relates to a formulation targeted at males, 66 years of age and over. This super senior male adult formula is a blend of dietary and endogenous micronutrients with appropriate increases of the relevant families of antioxidants to account for the increased needs of the super senior population.

In another further embodiment, the co-enzyme Q10 is increased from 30 mg to 60 mg; the n-acetyl cysteine is increased from 250 mg to 300 mg; and α-Lipoic acid is increased from 30 mg to 60 mg. In addition, L-carnitine (150 mg) may be added.

EXAMPLE 9

Suggested Daily Formulation

For women, the following supplements should be added:

| Calcium citrate | 1,500 mg |
|---|---|
| Magnesium citrate | 750 mg |
| Vitamin D | 100 I.U. |

Example 9 relates to a formulation targeted at females, 66 years of age and over. This super senior female adult formula is a blend of dietary and endogenous micronutrients with appropriate increases of the relevant families of antioxidants to account for the increased needs of the super senior population and with various additives such as calcium for proper bone health and bone density.

It will be understood that, in addition to antioxidant micronutrients, diet and lifestyle recommendations from healthcare professionals are also very important in maintaining optimal health and preventing disease risk. For example, in the diet, one should increase consumption of fresh fruits and vegetables; increase consumption of fiber (26 grams per day) from fruits, vegetables and fiber-rich cereals; avoid excessive calories; reduce consumption of food with high nitrate or nitrite content (e.g. preserved meats) and whenever eating such food, first consume antioxidants; avoid excessive amounts of charcoal-broiled or smoked meat or fish; reduce the consumption of pickled fruits and vegetables; reduce the consumption of caffeine containing beverages; and, for women 36 and older, consume a calcium rich diet.

Additionally, one should avoid drinking excessive amounts of alcohol; NOT SMOKE or chew tobacco and should avoid exposure to second hand smoke; exercise 3 to days a week for 30 minutes and, if doing aerobic exercise for 30 minutes of more, take antioxidant supplements beforehand; adopt a lifestyle of reduced stress; and avoid excessive sun exposure and use of UV light for skin tanning or hyperbaric oxygen "cocktails" for energy bursts.

In a further embodiment, the above mentioned base formulas and principle formulas can be modified and changed to address various specific problems such as radioactive treatments or exposure, heart disease, diabetes, cancer, traumatic brain injuries, stress disorders, hyperbaric oxygen exposure, smoking, Parkinson's disease, Huntington's disease, Alzheimer's disease, renal failure, chemical and other hazardous exposures, etc. There are also formulations for the active military personnel and veterans.

Example 10 below focuses on hearing health. For purposes of this invention, hearing health relates to noise induced and age related hearing loss, tinnitus and balance disorders.

EXAMPLE 10

Suggested Daily Formulation

| Vitamin A (Palmitate) | 5000 IU |
|---|---|
| Natural Vitamin E | 400 IU |
| (d-alpha Tocopheryl Succinate - 300 IU) | |
| (d-alpha Tocopheryl Acetate - 100 IU) | |
| Vitamin C (Calcium Ascorbate*) | 1500 mg |
| Vitamin $D_3$ (Cholecalciferol) | 400 IU |
| Vitamin $B_1$ (Thiamine Mononitrate) | 4 mg |
| Vitamin $B_2$ (Riboflavin) | 5 mg |
| Vitamin $B_3$ (Niacinamide Ascorbate*) | 30 mg |
| Vitamin $B_6$ (Pyridoxine Hydrochloride) | 5 mg |
| Folic Acid | 800 mcg |
| Vitamin $B_{12}$ (Cyanocobalamin) | 10 mcg |
| Biotin | 200 mcg |
| Pantothenic Acid (as D-Calcium Pantothenate) | 10 mg |
| Calcium Citrate | 250 mg |
| Magnesium Citrate | 125 mg |
| Zinc Glycinate | 15 mg |
| Selenium (Seleno-L-Methionine) | 100 mcg |
| Chromium (as Chromium Picolinate) | 50 mcg |

Plus 585 mg of a Proprietary Blend Containing:

| N-Acetyl Cysteine (NAC) | 300 mg |
|---|---|
| Coenzyme $Q_{10}$ | 60 mg |
| R-alpha Lipoic Acid | 60 mg |
| L-Carnitine | 150 mg |
| Natural Mixed Carotenoids | 15 mg |

*22 mg of Vitamin C is provided by Niacinamide Ascorbate

The hearing health formulation of the present invention has a two prong method of functionality: the first focuses on diminishing risk of hearing loss, balance disorders and tinnitus prior to exposure to hearing hazards and hearing loss related to aging; and the second focuses on mitigating hearing loss, balance disorders, tinnitus during or after exposure to the hearing hazard. In one embodiment and for purposes of this invention, hearing hazards are increased oxidative stress and acute and/or chronic inflammation produced by diverse groups of agents such as noise, vibration, cisplatin, gentamicin, aging, and Meniere's disease or any other factors that play a role in initiating and progression of hearing loss and disorders.

Example 11 below relates to ranges of the dosages and amounts of ingredients of the present invention:

EXAMPLE 11

Suggested Daily Formulation

Vitamin A (Palmitate) from about 3,000 to about 5000 IU
Vitamin E from about 50 to about 600 IU
   (d-alpha Tocopheryl Succinate—from about 50 to about 600 IU)
   (d-alpha Tocopheryl Acetate—from about 50 to about 300 IU)
Vitamin C (Calcium Ascorbate) from about 200 to about 800 mg
Vitamin $D_3$ (Cholecalciferol) from about 400 to about 600 IU
Vitamin $B_1$ (Thiamine Mononitrate) from about to 2 about 10 mg
Vitamin $B_2$ (Riboflavin) from about 2 to about 20 mg
Vitamin $B_3$ (Niacinamide Ascorbate) from about 5 to about 200 mg
Vitamin $B_6$ (Pyridoxine Hydrochloride) from about 2 to about 10 mg
Folic Acid from about 400 to about 1500 mcg
Vitamin $B_{12}$ (Cyanocobalamln) from about 5 to about 20 mcg
Biotin from about 100 to about 500 mcg
Pantothenic Acid (as D-Calcium Pantothenate) from about 5 to about 30 mg
Calcium Citrate from about 100 to about 500 mg
Magnesium Citrate from about 100 to about 300 mg
Zinc Glycinate from about 10 to about 40 mg
Selenium (Seleno-L-Methionine) from about 50 to about 300 mcg
Chromium (as Chromium Picolinate) from about 50 to about 200 mcg Blend:
N-Acetyl Cysteine (NAC) from about 100 to about 800 mg
Coenzyme $Q_{10}$ from about 20 to about 300 mg
R-alpha Lipoic Acid from about 15 to about 200 mg
L-Carnitine from about 100 to about 400 mg
Natural Mixed Carotenoids from about 5 to about 45 mg Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A hearing health formulation consisting of first and second compositions, said first composition consisting of:
   Vitamin A (Palmitate) from about 3,000 to about 5000 IU
   Vitamin E from about 50 to about 600 IU
   Vitamin C (Calcium Ascorbate) from about 200 to about 800 mg
   Vitamin $D_3$ (Cholecalciferol) from about 400 to about 600 IU
   Vitamin $B_1$ (Thiamine Mononitrate) from about to 2 about 10 mg
   Vitamin $B_2$ (Riboflavin) from about 2 to about 20 mg
   Vitamin $B_3$ (Niacinamide Ascorbate) from about 15 to about 200 mg
   Vitamin $B_6$ (Pyridoxine Hydrochloride) from about 2 to about 10 mg
   Folic Acid from about 400 to about 1500 mcg
   Vitamin $B_{12}$ (Cyanocobalamln) from about 5 to about 20 mcg
   Biotin from about 100 to about 500 mcg
   Pantothenic Acid (as D-Calcium Pantothenate) from about 5 to about 30 mg
   Calcium Citrate from about 100 to about 500 mg
   Magnesium Citrate from about 100 to about 300 mg
   Zinc Glycinate from about 10 to about 40 mg
   Selenium (Seleno-L-Methionine) from about 50 to about 300 mcg
   Chromium (as Chromium Picolinate) from about 50 to about 200 mcg,
   said second composition consisting of:
   N-Acetyl Cysteine (NAC) from about 100 to about 800 mg
   Coenzyme $Q_{10}$ from about 20 to about 300 mg
   R-alpha Lipoic Acid from about 15 to about 200 mg
   L-Carnitine from about 100 to about 400 mg
   Natural Mixed Carotenoids from about 5 to about 45 mg and
   wherein said formulation is designed to treat hearing hazards and hearing loss based on age.

2. The formulation of claim 1 wherein Vitamin E is selected from a group consisting of d-alpha Tocopheryl Succinate from about 50 to about 600 IU, d-alpha Tocopheryl Acetate from about 50 to about 300 IU and mixtures thereof, and wherein said mixed carotenoids are selected from a group consisting of natural sources of algae, alpha carotene, beta carotene, gamma carotene, lutein, lycopene, xynthines, beta-cryptoxanthin, zeaxanthin, astaxanthin, phytoene, canthaxanthin, fucoxanthin and mixtures thereof.

3. The formulation of claim 1 wherein said formulation is consumed by the user at least twice per day.

4. The formulation of claim 1 wherein said formulation is consumed by the user at a timing made for body tissue saturation prior to exposure to a hearing hazard, during exposure to a hearing hazard and for hearing loss caused by aging.

5. The formulation of claim 1 wherein said formulation is consumed by the user for long term maintenance after exposure to a hearing hazard, said long term maintenance is from about at least one week to about life long.

* * * * *